United States Patent
Belfer

(10) Patent No.: US 8,025,907 B2
(45) Date of Patent: Sep. 27, 2011

(54) COSMETIC COMPOSITION TO ACCELERATE REPAIR OF FUNCTIONAL WRINKLES

(76) Inventor: William A. Belfer, Ocean, NJ (US)

( * ) Notice: Subject to any disclaimer, the term of this patent is extended or adjusted under 35 U.S.C. 154(b) by 0 days.

(21) Appl. No.: 12/460,505

(22) Filed: Jul. 20, 2009

(65) Prior Publication Data
US 2009/0280078 A1 Nov. 12, 2009

Related U.S. Application Data

(62) Division of application No. 11/504,119, filed on Aug. 15, 2006, now Pat. No. 7,566,464.

(60) Provisional application No. 60/713,454, filed on Sep. 1, 2005.

(51) Int. Cl.
*A01N 65/00* (2009.01)
*A61K 31/74* (2006.01)

(52) U.S. Cl. ............... 424/725; 424/778; 424/78.03

(58) Field of Classification Search .............. None
See application file for complete search history.

(56) References Cited

U.S. PATENT DOCUMENTS

| | | | | |
|---|---|---|---|---|
| 5,470,874 | A | * | 11/1995 | Lerner |
| 6,471,972 | B1 | * | 10/2002 | Bonte et al. |
| 7,566,464 | B2 | | 7/2009 | Belfer |
| 2004/0132667 | A1 | * | 7/2004 | Lintner |
| 2004/0180102 | A1 | * | 9/2004 | Patt |
| 2006/0045894 | A1 | * | 3/2006 | Brown et al. |
| 2006/0045896 | A1 | * | 3/2006 | Morariu |
| 2008/0069912 | A1 | | 3/2008 | Demarne et al. |

FOREIGN PATENT DOCUMENTS

| | | | |
|---|---|---|---|
| FR | 2865131 | | 7/2005 |
| FR | 2865131 | A1 * | 7/2005 |
| JP | 08169816 | | 7/1996 |
| JP | 08169816 | A * | 7/1996 |
| JP | 2003171226 | | 6/2003 |
| JP | 2003171226 | A * | 6/2003 |
| WO | WO 2006080768 | A1 * | 8/2006 |

OTHER PUBLICATIONS

RD 474031 A1, Oct. 2003, RD, Unknown.*
www.hcbio.com.tw/pdf/Gatuline-Expression.pdf Gatuline Expression.
MINTeL gnpd, Cellu-Age Therapy Instant Lifting Serum, Jan. 2006.
AddiActive No. 1, Gattefossé Group, Spring Summer 2005.
Gatuline® Expression: Fast Track Smoothing, Gattefossé Group, Apr. 2005.
Matrixyl™ 3000 Sales Brochure, Seraderma Inc., Jan. 2005.
In-Cosmetics Trade Show Directory, Berlin, Germany, Apr. 12-14, 2005.
U.S. Appl. No. 11/504,119, filed Aug. 15, 2006.
U.S. Appl. No. 60/713,454, filed Sep. 1, 2005.
Affidavit of Frédéric Demarne.
Final Office Action mailed Feb. 4, 2009 in connection with U.S. Appl. No. 11/504,119.
Non-final Office Action mailed Oct. 8, 2008 in connection with U.S. Appl. No. 11/504,119.
Amendment and Response filed Nov. 14, 2008 in connection with U.S. Appl. No. 11/504,119.
Interview Summary mailed Mar. 9, 2009 in connection with U.S. Appl. No. 11/504,119.
Amendment and Response filed Mar. 16, 2009 in connection with. U.S. Appl. No. 11/504,119.

* cited by examiner

*Primary Examiner* — Michele Flood
(74) *Attorney, Agent, or Firm* — Robert M. Skolnik

(57) ABSTRACT

A cosmetic composition consists of a combination of peptides that regenerate the dermal matrix and a rapid acting muscle relaxant derived from the extract of the plant, *Acmella oleracea*. By limiting cutaneous deformation caused by the contraction of facial muscles the extract increases the efficiency of the peptides in reducing expression lines.

6 Claims, 2 Drawing Sheets

COSMETIC COMPOSITION TO ACCELERATE REPAIR OF FUNCTIONAL WRINKLES

CROSS-REFERENCE TO RELATED APPLICATIONS

Applicant claims priority of U.S. Provisional Patent Application 60/713,454, filed Sep. 1, 2005. This application is a division of U.S. patent application Ser. No. 11/504,119, filed Aug. 15, 2006, now U.S. Pat. No. 7,566,464, issued Jul. 28, 2009.

FIELD OF INVENTION

The present invention relates to the use of compositions that are designed to prevent and heal wrinkles in sun-damaged or aging skin caused by facial expression, otherwise known as expression lines.

DESCRIPTION

Background of the Invention

The following prior art references are cited in this application.

| U.S. Patents | | |
| --- | --- | --- |
| D/N 20040132667 | Lintner | |
| 6,919,072 | Varni, et al. | Jul. 19, 2005 |
| 6,908,925 | Breton, et al. | Jun. 21, 2005 |
| 6,906,036 | Quirk, et al. | Jun. 14, 200 |
| 6,884,425 | Breton, et al. | Apr. 26, 2005 |
| 6,866,856 | Lu, et al. | Mar. 15, 2005 |
| 6,861,078 | Pauly, et al. | Mar. 1, 2005 |
| 6,858,212 | Scholz, et al. | Feb. 2, 2005 |
| 6,846,812 | Dalko, et al. | Jan. 25, 2005 |
| 6,809,075 | Mitts, et al. | Oct. 26, 2004 |
| 6,794,362 | Sandberg | Sep. 21, 2004 |
| 6,777,389 | Mitts, et al. | Aug. 17, 2004 |
| 6,620,419 | Lintner | Sep. 16, 2003 |
| 6,531,132 | Paufique | Mar. 11, 2003 |
| 6,492,326 | Robinson, et al. | Dec. 10, 2002 |
| 6,461,857 | Scholz, et al. | Oct. 8, 2002 |
| 6,444,647 | Robinson, et al. | Sep. 3, 2002 |
| 6,344,461 | Breton, et al. | Feb. 5, 2002 |
| 6,335,368 | Liviero, et al. | Jan. 1, 2002 |
| 6,224,850 | Breton, et al. | May 1, 2001 |
| 6,169,074 | Montal, et al. | Jan. 2, 2001 |
| 6,069,129 | Sandberg, et al. | May 30, 2000 |
| 5,976,559 | De Lacharriere, et al. | Nov. 2, 1999 |
| 5,869,068 | De Lacharriere, et al. | Feb. 9, 1999 |
| 5,830,708 | Naughton | Nov. 3, 1998 |
| 5,547,997 | Kludas | Aug. 20, 1996 |
| 5,198,465 | Dougardi | Mar. 30, 1993 |
| Foreign Patents | | |
| EP1180524 A1 | EP | |
| 2865131 | Fr | |
| 0108433 | Fr | Jun. 26, 2001 |
| DE-PS 20 | Gr | |

OTHER REFERENCES

Thalmann et al. "A Computational Skin Model: Fold and Wrinkle Formation", pp. 1-5 (Internet access at: www.miralam.unique.ch/papers/160.pdf)

Lintner K, Preschard, O. "Biologically Active Peptides: From A Laboratory Bench Curiosity to a Functional Skin Care Product", International Journal of Cosmetic Science, 22, 207-218 (2000)

Mas-Chamberlin et al. "Matrikines: A Natural Concept to Replace Retinoids in Wrinkle Treatment, Personal Care Asia Pacific, 5, 1, (2004).

Duke, J. A. CRC Handbook of Medicinal Herbs, CRC Press, Boca Raton, Fla., 1985, 110-1

Carruthers et al. "Botulinum Toxin in the Treatment of Glabellar Frown Lines and Other Facial Wrinkles" in Therapy with Botulinum Toxin (Jankovic et al. eds.) Ch. 46: 577-595 (1994).

Lowe, N., et al. "Pharmacology of Retinols In Skin", Vol. 3 pp. 240-248 (1989)

Oikarinen, "The Aging of Skin: Chronoaging Versus Photoaging", Photodermatal. Photoimmunol. Photomed., Vol. 7, pp 3-4 (1990)

"MatrIxyl. In vivo Anti-wrinkle Test On Volunteers Using Retinol" Sederma research publication, October 2000, Vol. 1), Boissieux, L. et al., "Simulation of Skin Aging and Wrinkles with Cosmetic Insight", pp. 1-11, Proceedings of Eurographics Workshop on Animation and Simulation (EGCAS 2000), Interlaken, Aug. 21-22, 2000.

Consumers are increasingly seeking "anti-aging" products that treat wrinkling, creasing and furrowing of the skin. The advent of costly and painful cosmetic injections for treating expression lines of the face has heightened interest in finding topical alternatives that are effective and non-invasive.

Expression lines are a distinct type of wrinkle that occurs on the facial skin at an early adult age. They are related anatomically to the facial expression muscles in the periorbital, glabella, forehead, and perioral areas. The activity of these muscles during the actions of smiling, squinting, pursing of the lips, and frowning places greater physical stress upon the overlying skin than in other areas in the face. For this reason expression lines are less responsive to those topical treatments that focus upon the non-contractile elements of cutaneous anatomy, such as the epidermis. In order to be most effective treatment of expression lines should also entail the inhibition of the facial expression muscles and the muscle fiber elements associated with the dermis. A myriad of substances that relax striated muscle fibers are described in the cosmetic prior art. The problem is that the muscle relaxants of the prior art are either slow acting, they are not potent enough, or the inhibitory effects are not cumulative. Furthermore, none of these muscle relaxants reduce facial muscle actions. A newly discovered plant extract that rapidly inhibits deformation of the dermis enables substances that repair and rejuvenate it to become more effective.

An expression line is formed when a muscle of facial expression contracts or shortens itself beneath the skin and then relaxes and returns to its resting length. The skin can also shorten and rebound, but not as well as the muscle. Therefore, the skin tends to buckle and fold inward as the muscle contracts. The ability of the skin to withstand the shortening and rebounding of the underlying muscle is related to the quality and health of the upper dermis. With increasing age the thickness, elasticity, collagen content. and reparative ability of the dermis diminishes. The skin can no longer rebound from this action and the fibrous intercellular matrix of the dermis weakens and breaks. At this point the skin has developed a permanent wrinkle. The wrinkle will continue to deepen as this area of the skin is subjected to the perpetual stress of facial expressions.

Anatomy of Expression Lines

The skin associated with expression lines is different histologically from that found elsewhere in the face. The interlobular septa of the sub-dermal connective tissue contains striated muscle tissue fibers (panniculus carnosus). These fibers arise from the underlying facial muscle groups. They are integrated within the collagenous network of the lower (reticular) dermis. A sub-population of dermal fibroblasts in the upper (papillary) dermis, known as "myo-fibroblasts", have inherent contractile characteristics similar to striated muscle tissue. Contractions within these dermal fibroblasts are mediated by the same neurotransmitter, i.e. acetylcholine, as the fiber elements of striated muscle.

Muscle fibers within the facial skin have a direct influence on its surface smoothness, and modulating the neural motor influx to these muscle fibers causes a reduction of wrinkles. For example, patients who suffer from Bell's palsy of the facial nerve have smoother skin on the paralyzed side of the face than on the non-paralyzed side. Also, Botox™ cosmetic injections not only immobilize the forehead and upper eyebrow muscles, but they also smooth the skin external to these muscles. Botox™ interferes with the uptake of acetylcholine within the synaptic junction of the afferent motor neuron of muscle fibers, thereby preventing contraction of muscle tissue associated with wrinkles and furrows. Botox™ treatment is in high demand, and thus it is the goal of cosmetic scientists to develop a topical equivalency (see A. Blitzer et al., Arch. Otolaryngol. Head Neck Surg., 119, pages 1018 to 1022 (1993)) (see J. D. Carruthers et al., J. Dermatol. Surg. Oncol., 18, pages 17 to 21 (1992).

Muscle Relaxants

The causal relationship of muscle tissue to wrinkle formation has moved cosmetic scientists to formulate substances that block the propagation impulses to the muscle-neuron junction, thereby relaxing wrinkles. Some of these are known as channel blockers, and they interfere with the transmission of nerve impulses upstream of the neuromuscular junction. Several inventors teach the use of calcium channel blockers or agonists of the chlorine channel that slow the transmission of nerve impulses to the skeletal muscle fibers that are integrated within the skin. These agents slow transmission of impulses to the neuromuscular junction by inhibiting the exchange of ions across the cell membrane of afferent neurons. Brenton, et al. (U.S. Pat. No. 6,908,925) (U.S. Pat. No. 6,344,461) discloses a calcium channel influx inhibitor, Verapamil. Also, Liviero, et al. (U.S. Pat. No. 6,335,368) teaches that the calcium channel blocker Alverine reduces muscle fiber contractibility in skin wrinkles. Both of these patents employ an in vitro model (phrenic nerve and diaphragm muscle) to show how channel blockers intervene on the neuromuscular junction (neuron to muscle fiber connection) to prevent muscle stimulation. However, this experimental model does not represent the environment, as it exists in living skin. De Lacharriere et al, (U.S. Pat. No. 5,976,559) (U.S. Pat. No. 5,869,068) and Breton, et al. (U.S. Pat. No. 6,224,850) discuss chlorine channel agonists that have wrinkle relaxing properties, but no test data is provided to show how effectively they inhibit muscle contraction.

Other muscle relaxants are substances that interfere with acetylcholine uptake upon receptor sites on the muscle cell membrane. The histological characteristics and molecular exchange that takes place at the synaptic junction of the nerve to muscle junction is referred to as the SNARE Complex and the substances that interfere with acetylcholine availability are referred to as having "anti-cholinergic" properties. Lu, et al. (U.S. Pat. No. 6,866,856) recently discovered alkaloid extracts of citrus fruits known as limonoids, (toosendanin and azadirachtin) that inhibit acetylcholine release at the neuromuscular junction of skeletal muscle. Lu et al. do not provide data on the rate of adsorption through the skin and the rapidity of the relaxation response.

Montal, et al. (U.S. Pat. No. 6,169,074) describes combinations of three peptides that bind together and then interfere with the SNARE complex within the synaptic gap on the neuromuscular junction. This occurs via the ability of the peptide to act as a receptor for docking of synaptic vesicles that would otherwise release acetylcholine onto the muscle cell membrane. This peptide complex is purported to be a substitute for Clostridium neurotoxin (Botox™) except that the suppression of neurotransmitter released at the neuromuscular junction is not much more than 50%. Therefore, the inventors' claim that this peptide can be a substitute for an injectible Clostridium neurotoxin may be an exaggeration.

Notwithstanding, Blanes, et al. (EP1180524 A1) disclose the invention of peptides that are able to "at least partially" inhibit acetylcholine release within the SNARE complex. The principle molecule, acetyl hexapeptide-3, (marketed as Argireline® by Lipotec, SA) is claimed to be a topical alternative to Botox® cosmetic. However, clinical experience with this agent does not match the Blane et al. in vivo data. After factoring the influence of the cosmetic base ingredient in their in vitro study, wrinkle depth reduction by the hexapeptide component is less than 30% after thirty days. (see Blanes-Mira, et al., "A Synthetic Hexapeptide (Argireline) With Anti-wrinkle Activity", International Journal of Cosmetic Science, vol. 24, pp 303-310, 2002). Without a palmityl or myristyl tail on this peptide, conventional formulations of acetyl hexapeptide-3 can be expected to lack suitable penetration.

Another myo-inhibitory substance used in treating expression lines is a recently synthesized copy of the Walgerin 1 molecule which is responsible for the paralytic effects of the Temple viper, (Tropidolaemus wagleri) venom The substance (marketed by Pentapharm, Ltd., Switzerland) has been identified by the chemical name Dipeptide Diaminobutyroyl Benzalamide Diacetate. It has potent anti-cholinergic action upon the cholinergic receptor sites at the post synaptic membrane of the neuromuscular junction. Though in vivo studies have shown that it suppresses contractile activity in cultured muscle tissue within two hours, clinical tests have shown it takes 28 days to reduce forehead expression lines up to 52%.

As with all topical delivery systems the rate and depth of skin penetration affects the dose administered to the site. Prior art formulations that were labeled as wrinkle relaxants, myo-relaxants, or "Botox™-like effects" are not backed by published data that support the argument that these topical applications behave with nearly the efficacy as their pharmacological derivatives. The exception may be gamma amino butyric acid (GABA), a brain neurotransmitter that has a fast initial onset but short muscle suppression. As will be discussed elsewhere in the application, a novel plant isolate, spilanthol, (the active isolate of *Acmella oleracea* extract) has proven to be the most rapid acting topical muscle relaxant to date. While the physiology of its action upon muscle is not yet known, it has been shown to have rapid and progressive muscle relaxing ability even at very small percentages. This molecule inhibits micro-muscle fibers within cutaneous tissue, but more significantly, it reduces the twitch reflex of the facial expression muscle itself. The applicant has found it to be clinically superior to muscle relaxants of prior art. The applicant has carried out electromyographic tests using surface sensors placed upon the frontalis muscle (Thought Technology, Ltd., USA.; Myoscan Pro EMG sensors, Procomp Plus Biofeedback instrument. and Biograph software, recorded on an IBM Pentium 4 laptop computer). The tests show that following application of a composition of 6.0% *Acmella oleracea* extract in a generic base there a decrease in action potential generated by this expression muscle both at rest and during voluntary contraction. The muscle suppression lasts for nearly 8 hours. Accordingly, *Acmella oleracea* extract is the preferred muscle relaxant of this application.

Although the physiology of neuromuscular inhibition is well understood in the prior art, it is necessary to point out that many pharmaceuticals and natural extracts are less efficient when they are not used according to their intended route of administration. Unfortunately, many of the substances of the prior art are compositions that are normally given by ingestion or injection. They may be far less effective when they are administered as topical agents. Accordingly, observations in the prior art that are based on in vivo testing should be validated for efficacy in vitro. The *Acmella oleracea* extract in its native form is used as a topical muscle relaxant by native cultures in the eastern African countries, and therefore it has been experienced outside of the laboratory in its normal usage.

Dermal Repair

The regenerative ability of the dermis has a critical bearing on its ability to withstand the chronic muscle contraction and relaxation of the expressive muscles. As a consequence of aging or sun damaged skin there is a reduction in the fibroblastic cells and blood vessels that are needed to rejuvenate the lower dermis. Fibroblasts in the "basal layer" of the upper dermis replicate into new cells more slowly, they loose their capacity to manufacture collagen, and they are less able to organize and preserve the collagen fiber network. Since the dermal matrix is the source of collagen and major water holding molecules, i.e. the glycoaminoglycans and hyaluronic acid, preserving it is essential to the health of the epidermis as well. Without continual replenishment of precursor proteins, disorganization and dissolution of the collagen fiber network and the extra-cellular matrix takes place. The result of this process is a flattening of the dermal-epidermal junction and a weakening of the mechanical resistance of the upper dermis. Thus, the aging skin has a much greater susceptibility for temporary deformations—that occur during facial expression—to be come permanent. (see Oikarinen, "The Aging of Skin: Chronoaging Versus Photoaging," Photodermatol. Photoimmunol. Formation, Photomed., vol. 7, pp. 3-4, 1990). (see Thalmann et al. "A Computational Skin Model: Fold and Wrinkle Formation", pp. 1-5).

There are several teachings in the art (U.S. Pat. No. 6,794, 362) (U.S. Pat. No. 6,777,389) that discuss singular molecules or compositions thereof for enhancing the elasticity of skin or strengthening the dermis. They are formulated from peptides or peptide-like compounds that mimic the molecular composition of elastin or add to it. Mitts, et al. (U.S. Pat. No. 6,809,075) postulated that a peptide/retinoid composition could integrate within the elastin component of the dermis, a thereby increasing the ability of the skin to rebound from deformation. More often the prior art teaches that natural or synthetic peptide formulations can enhance the collagen fiber network or extra-cellular substrate of the dermal matrix. Hence, a novel integrity (Lowe, N. et al., *Pharmacology of Retinols In Skin", Vol. 3 (1989), pp. 240-248). However, the instability and irritation caused by retinoids are problematic. approach advocated by Doguardi (U.S. Pat. No. 5,198,465) is to increase the collagen content in the skin in general by the topical application of synthesized precursor collagen molecules and coenzymes of the collagen metabolic pathway. The premise is that direct replacement via diffusion and adsorption of precursor molecules fortifies deficient skin. A similar notion taught by Kludas (U.S. Pat. No. 6,906,0360) is that a substantially natural composition can have a reparative and remodeling effect at the dermal-epidermal junction. Also, recent art (U.S. Pat. No. 6,906,036) (U.S. Pat. No. 6,884,425) has taught that inhibitors of matrix metalloprotienases are capable of preventing the disruption of the dermis, healing it and facilitating a return to normal healthy skin. None of the aforementioned patents teach the capacity to stimulate fibroblastic activity and synthesis of collagen precursors; nor do they profess to restore dermal thickness and collagen fiber network.

There is universal acknowledgement of the value that retinoid substances have in improving epidermal and dermal function.

In a recent patent Varni, et al. (U.S. Pat. No. 6,919,072) identifies a composition of a retinoid and a matrix metalloproteinase inhibitor that inhibits collagen breakdown, promotes collagen at the content by increasing procollagen synthesis, increases keratinocytes and fibroblastic proliferation. The invention restores the thickness of the epidermal-dermal interface in chronologically aged skin and it restores collagen content within the upper dermis to normal levels. Therein lies its property to give the skin strength to withstand environmental and physical stress. As with other retinoids, the retinoid of Lowe requires prolonged application and the dermal repair is much slower than with the preferred embodiment of this application.

The Significance of Peptides

The focus of the early art has been on disclosing substances that were thought to physically replenish the molecules that build new collagen or that add substances which irritate or disrupt the basal layer to effect its regeneration and healthy reconstitution. More recent art teaches the benefits of topical peptide treatments in stimulating the upper dermis to renew itself by cellular re-growth. This has is supported by the knowledge that the body has naturally occurring peptides that are instrumental in stimulating the healing process following a wound to the skin.

Robinson teaches (U.S. Pat. No. 6,492,326) various formulations containing combinations of palmitoyl pentapeptide-3, derivatives of pentapeptides, and mixtures thereof. Lintner (U.S. Pat. No. 6,620,419) discloses peptide formulas of the general sequence palmitoyl-lysyl-threonyl-lysyl-serine that increase the synthesis of collagen and gylcosaminoglycans. They act synergistically to heal wrinkles and other forms of skin aging far more effectively than earlier formulations. The key difference in the Lintner teaching to that of Robinson is the addition of a fatty acid chain onto the terminal end of a pentapeptide that makes this lipophilic modified peptide very efficient at penetrating the epidermis and thus more effective reaching the formative layers of the dermis. The Lintner patent is the basis for the commercial product Matrixyl® (Sederma, SA). By virtue of published research Matrixyl™ is recognized as a cosmetic substance that increases and restores the formative cells, fibro-collagenous network and extra-cellular components. (Lintner K, Preschard, O., "Biologically Active Peptides: From A Laboratory Bench Curiosity to a Functional Skin Care Product", International Journal of Cosmetic Science, 22, 207-218 (2000)) and (Mas-Chamberlin et al. "Matrikines: A Natural Concept to Replace Retinoids in Wrinkle Treatment, Personal Care Asia Pacific, 5, 1, (2004). The net result is to increase the thickness of the skin by restoring the reparative capacity of the upper dermis. Consequently, the skin is better able to withstand the deformation imposed on it by the active contraction and relaxation of expression muscles, and micro-contractions within the skin itself. While the magnitude of skin smoothness is good with Matrixl™ and surpasses the retinoids (see "Matrlxyl. In vivo Anti-wrinkle Test On Volunteers Using Retinol" Sederma research publication, October 2000, vol 1), it is far less effective than Matrixyl™3000.

The latest peptide formulations to appear in the art, i.e., the oligopeptides, tetrapeptides and tripeptides are described by Lintner in (US Publication #20040132667), and are marketed by Sederma, SA. as Matrixyl™ 3000. Matrixyl™ 3000 is defined as a mixture of Glycerin, water, butylene glycol, carbomer, polysorbate and palmitoyl oligopeptide and palmitoyl terapeptide in the INCI classification. While this patent describes a multitude of possible active ingredients and applications for this invention Lintner does not identify one ingredient that is a striated muscle relaxant. The source that Lintner uses to create a list of possible additional ingredients of the present invention is "The CTFA Cosmetic Ingredient Handbook, Ninth Edition (2002)" was published prior to the disclosure of the muscle relaxant property of the *Acmella oleracea* plant and could not have been Lintner's intention to include as an additional ingredient in (US Publication 20040132667). Furthermore, the plant extracts that Lintner teaches in this patent are "vegetable or marine", and neither characterizes the *Acmella oleracea* plant, or botanically derived extracts from deciduous trees, e.g. *Fagus sylvatica* or *Juglans regia*. According to published clinical data by Sederma, SA., Matrixyl™ 3000 is much faster at reducing wrinkles then the original Matrixyl™ formula, and hence it is the critical peptide of this invention. Although not disclosed by Lintner in published literature, presumably the dermal regenerating mechanism for Matrixyl™ 3000 is the same as Matrixyl™, but the lesser efficacy of the palmitoyl pentapeptide product has to do with the larger molecular size and penetrability to dermis layers.

De Lacharrier, et al. (U.S. Pat. No. 5,976,559) identifies several amino acids that are chlorine channel agonists and slow the transmission across afferent neurons that impulse cutaneous muscle fibers. Principle among these muscle relaxants is gamma-aminobutyric acid (GABA). This patent is significant to this applicant's invention because it teaches that GABA and subunits of the GABA receptor site, i.e. a benzodiazepine, a steroid, and a barbituate, can be combined with mixtures of retinoids—a-hydroxy acid and beta hydroxy acid—to improve collagen synthesis. Other generally known actions of GABA are inhibition of striated muscle, the effect on collagen and cell renewal, and inhibition of elastase. Also, (JP-A-05043448) claims that the combination of GABA and diisopropylamine, a collagen precursor, can be used synergistically to prevent cutaneous aging. Finally, Dalco, et al (U.S. Pat. No. 6,846,812) shows a topical compound comprised of the steroid 7-Oxo-DHEA (7-oxo-dehydroepiandrosterone) and an effective amount of at least one other active agent among a comprehensive list of dermal and epidermal stimulants. It is significant to this application that Dalco teaches the inclusion of the palmitoyl pentapeptide-3, specifically Matrixyl™, being formulated together with muscle relaxants. However, the muscle relaxants that may be included are calcium inhibitors, chlorine-channel openers, and the acetylcholine inhibitor—specifically identified as the hexapeptide Argireline™ (marketed by Lipotec, SA). These muscle relaxants will not speed the dermal stimulation of peptides. They have not demonstrated rapid muscle relaxation effects. Also, the basis of the patent is the inclusion of the steroid 7-Oxo-DHEA; and the interdependence between the peptide and muscle relaxant is not taught.

SUMMARY OF THE INVENTION

Hitherto, most cosmetic compositions for treatment of expression lines focused on either strengthening the dermis, or inhibiting the muscle tissue that influences this type of wrinkle. A synergistic composition focused specifically on healing expression lines has not been taught to this applicant's knowledge. Furthermore, the recent peptide formulations, (US Publication #20040132667) (U.S. Pat. No. 6,620,419) (U.S. Pat. No. 6,492,326) that service many types of skin disorders, in themselves can not reach the same level of efficacy when treating expression lines without the addition of a potent muscle relaxant ingredient as claimed herein.

The hypothesis applied to this application originates from universal knowledge about the wound healing process within collagenous elements of mammalian tissues, and in particular, external skin. During cutaneous wound healing the collagen fibers within the injured dermis reorganize and repair best when they are not subjected to disruptive movement or under contractile tension. Furthermore, mechanical stimulation of dermis cells causes them to secret more elastase and collagenase, and this reduces the skin's ability to generate collagen fiber precursors.

The object of the present invention is to provide the most favorable environment within which compositions for rejuvenating the dermis can have maximum effect. In order for the healing of expression lines to take place in the fastest manner, the contractibility of muscle fibers must be suppressed quickly, and intensely, over a sustained period of time. Once this condition is met repair of the dermal matrix can occur with efficient delivery of matrix stimulating peptides. However, these peptides must be capable of stimulating fibroblasts to produce matrix protective enzymes, and prevent the breakdown of matrix fibers, fiber constituents, and pre-fiber proteins.

The present invention is a topical cosmetic composition containing a safe and effective amount of an extract of *Acmella oleracea* that is mixed with commercially available formulations that contain as a critical component the active peptide or peptides selected from groups of dermal rejuvenating peptides as described herein. The extract of the plant *Acmella oleracea* is the critical component of the present invention that rapidly relaxes the contractile muscle elements and suppresses the action of the expressive facial muscle. The preferred peptides mentioned herein are the constituents that rejuvenate the dermal matrix. The inclusion of a fast acting muscle relaxant that reduces the physical stress upon the upper dermis accelerates the dermal healing of the expression lines taking place by the action of the peptides. The mixture is combined within an inert cosmetic base suitable for topical application to the skin.

Other active skin care ingredients may be added to this composition that have supportive actions and impact upon the upper dermis, dermal matrix, as well as the epidermis, but themselves do not initiate the critical effects upon the dermis or muscle tissue as taught in this invention. They are provided to: effect an increase penetration of ingredients into the skin, as adjunctive anti-cholinergic peptide(s), as anti-oxidant(s), as an anti-inflammatory, as a dermal matrix precursor(s), as a skin circulation promoter, as vitamins, as moisturizers, as skin softeners, as wrinkle preventives, as botanical dermal matrix builders, as skin whiteners, as sunscreens, as metalloproteinase inhibitors, and as healing agents.

The *Acmella oleracea* extract has critical importance to this art (Fr 2865131, publication date Jul. 22, 2005 issued to Gattefosse® Group, France). The active isolate identified as having the myo-inhibitory quality is the molecule, spilanthol.

In vitro, a 0.6% concentration by volume of the extract blocks muscle contractions rapidly; and a 1.2% concentration sustains it over a 24 hour period. In vitro, the magnitude of the effectiveness is dose dependent. A 2% concentration showed a consistent wrinkle smoothing effect in vivo after 24 hours and this continued to increase over the next 28 days. To date the mechanism of action has not been described, however, due to its fast action it is likely to work directly on the motor neuron (source literature by Gattfosse, SA).

An important teaching of this present application is that repair of the dermal matrix by Matrixyl™ 3000 is faster and more durable when facial expression induced flexion of the skin is minimized.

An important teaching of this present application is that repair of the dermal matrix by Matrixyl™ 3000 is faster and more durable when muscle tension within the dermis is minimized.

An important teaching of this present application is that this formulation accelerates the improvement in the physical appearance of the expression lines.

Another teaching is that the duration and intensity of the muscle relaxation has a major influence on the speed and quality of the expression line repair.

Another important premise of this invention is that the muscle relaxant of the composition should be synergistic with the dermal stimulating peptide, Matrixyl™ 3000.

An equally important teaching of this art is the requirement that compositions used to heal the expression lines, as opposed to temporarily suppression them, shall restore the cellular mechanisms for rejuvenating, strengthening, and thickening the dermis more efficiently by reducing mechanical deformation of the skin.

Another important object of this teaching is that the two mechanisms needed for the most effective means of resisting mechanical stress that cause expression lines are: (1) suppression of muscle contractibility of the muscles of facial expression, and (2) the physiological rejuvenation, strengthening and thickening of the dermal matrix.

Another object of this teaching is that consistent use of this composition shall prevent reflex expression muscle contractions from causing permanent expression lines.

Another important teaching of this art is that in order for the healing of expression lines to take place most effectively the muscle relaxant component of the composition should have a progressively greater muscle relaxing effect over time and thus be synergistic with the component intended on dermal matrix building.

Another important teaching of this art is that the ideal muscle relaxant used in compositions for reducing expression lines has a fast mode of action.

These and other objects are accomplished by the present invention that provides a method and composition for the topical treatment of expression lines.

DETAILED DESCRIPTION OF THE PREFERRED EMBODIMENTS

Figure 1:
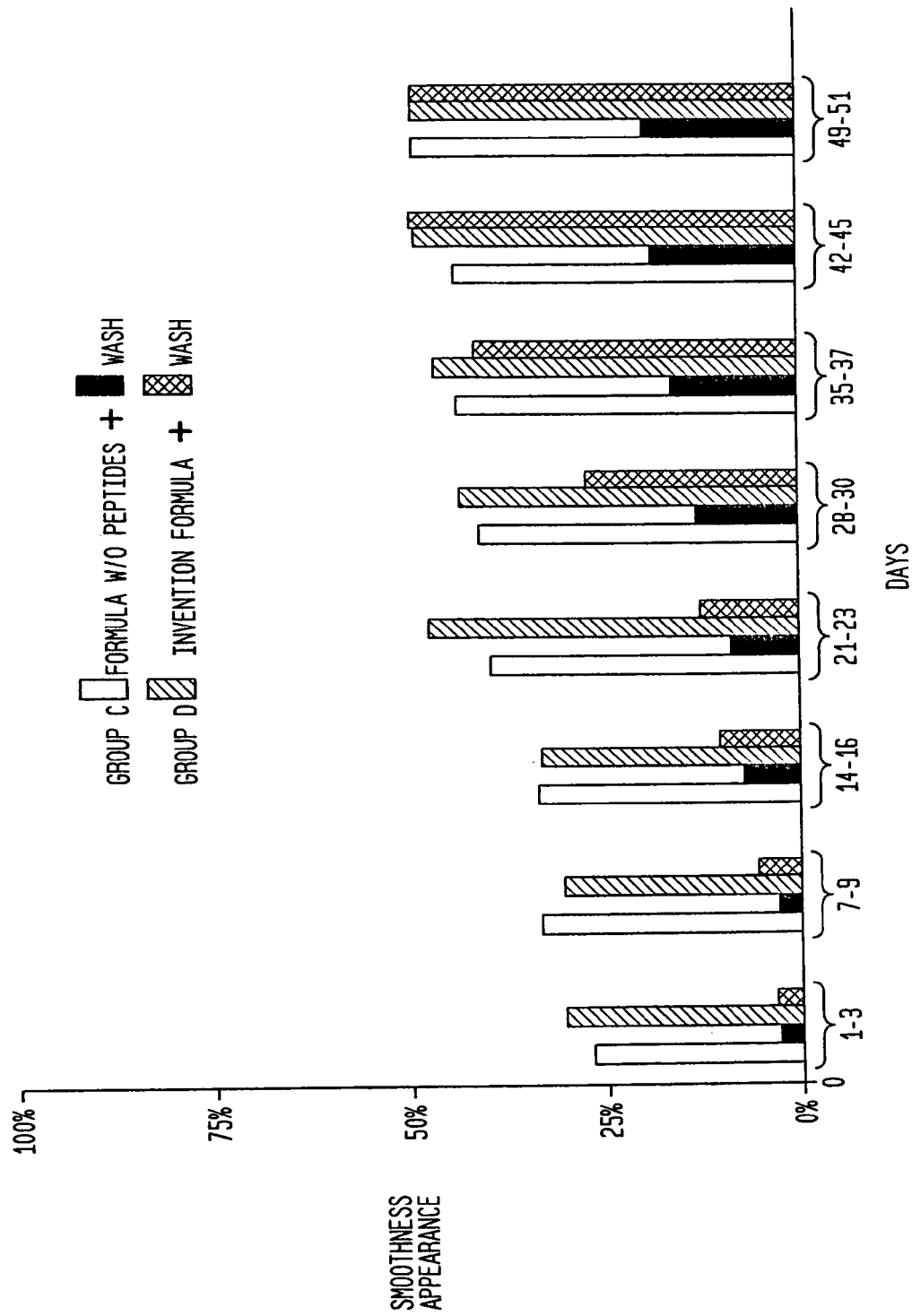
FIGS. 1-2 are graphs showing the test results obtained with use of the present invention.

The invention formulated herein contains an effective amount of the hydroethanolic extract of *Acmella oleracea*; preferably contains an effective amount of the peptide formulation known as Matrixyl™ 3000 (Sederma SA), therein containing palamitoyl oligopeptides, palmitoyl tetrapeptides and palmitoyl tripeptides; and one or more active agents in a dermatologically acceptable carrier that is applied to affected skin areas.

The extract *Acmella oleracea* is commercially available from Gattefosse, France and marketed under the name Gatuline® Expression. Gatuline® Expression is the hydroethanolic extract of the subtropical plant *Acmella oleracea*. This extract is available in solution form within water and ethanol, thus enabling it to be mixed homogenously into the peptide base formulations as described herein. The extract is active in compositions having a pH range of between 3 and 10.

The *Acmella oleracea* extract is preferably present in the invention at concentrations of from about 0.01% to about 20%, more preferably from about 0.1% to about 10%, and most preferably from about 0.5% to about 6%. The herein described peptide compounds are preferably present in the invention at concentrations of from about 0.01% to about 20%, more preferably from about 0.1% to about 10%, and most preferably from about 0.5% to about 6%.

The preferred peptides are contained within a preferred commercial composition consisting of an effective concentration of Matrixyl™ 3000 (commercially available from DeWolf Chemical, USA). Matrixyl™ 3000 is a formulation of the preferred peptides: palmitoyl tetrapeptide (N-palmitoyl-Gly-Gln-Pro-Arg (SEQ ID NO: 3) and derivatives thereof; palmitoyl tripeptide (N-palmitoyl-Gly-His-Lys) and derivatives thereof; and peptides within the group of peptides known as oligopeptides.

In preferred embodiments of the present invention the resulting composition preferably contains Matrixyl™ 3000 from about 0.01% to about 50%, more preferably from about 0.05% to about 20%, and even more preferably from about 0.1% to about 10%, by weight.

In other embodiments of the present art a less preferred dermal stimulating peptide is Matrixyl™ (marketed by Sederma, SA). Matrixyl™ is a palmitoyl pentapeptide. It has similar dermal stimulating properties to the more recent albeit faster acting Matrixyl® 3000. In all embodiments of the present invention the resulting composition less preferably contains Matrixyl™ from about 0.01% to about 10% by weight.

In still other embodiments of the present art a less preferred dermal stimulating peptide is SYN®-COLL (marketed by Pentapharm, Ltd Switzerland). SYN®-COLL is palmitoyl tripeptide-3. It has similar dermal stimulating properties to the more recent albeit faster acting Matrixyl™ 3000. In all embodiments of the present invention the resulting composition less preferably contains SYN®-COLL from about 0.01% to about 10% by weight.

In all embodiments of the present invention at least one additional skin care active is present in the composition. The preferred additional ski care active is dipeptide diaminobutyroyl benzalamide diacetate. In all embodiments of the present invention the resulting composition preferably contains dipeptide diaminobutyroyl benzalamide diacetate from about 0.01% to about 5.0%.

A preferred commercial composition containing the aforementioned critical peptide formulation of Matrixyl™ 3000 and additional skin care actives, herein referred to as a "matrix repair serum," is manufactured by Dermastart, Inc., Clermont, Fla. under license of Sederma, SA. The herein dermal matrix repair serum also contains these additional skin care actives: aloe vera gel, green tea extract, marine collagen, dexapanthenol, hydrolyzed wheat protein, *Centella asiatica*, allantoin, acetyl hexapeptide-3, chitosan and phenoxyethanol.

The matrix repair serum contains from 0.01% to about 10% volume, more narrowly about 5%, Matrixyl™ 3000; from about 1% to about 5% volume, more narrowly about 2%, *Centella asiatica*; from about 1.0% to about 10.0% weight %, more narrowly about 3.0%, hydrolyzed wheat protein; from about 0.5 to about 2.0 weight %, more narrowly about 1.5%, allantoin; from about 1% to about 2% weight % dexapanthenol or pantothenic acid; from about 1 to about 3 weight %, more narrowly about 3% acetyl hexapeptide-3; and from about 1 to about 3 weight 20%, more narrowly about 3%, marine collagen.

In other embodiments of this invention at least one other of the following skin care actives may be added to enhance the overall efficacy of the invention. These are: superoxide dismutase, Vitamin A (retinoids and derivatives thereof), Vitamin B3 (Niacin), Vitamin C, Vitamin E, Lycopene, pycnogenol, Vitamin K and/or hibiscus flower extract may be added when the formulation is designed for eye creams or gels that are required when circulatory deficiencies are present. In still other embodiments Pycnogenol may be added to replace or supplement green tea as an anti-oxidant. Fagus sylvatica (from Gattefosse, SA) extract may be added as an additional smoothing and moisturizing agent where dryness and thinness of the skin is associated with the emergence of expression lines. Another embodiment may include Water Lily extract to increase barrier protection. *Jugans regia* (from Gattefosse, SA) seed extract may be added to an embodiment that focuses on preventing the emergence of premature expression lines when mechanical distortion of the skin is apparent, but permanent creasing has not yet resulted. Lecithin may replace hydrolyzed wheat protein to enhance moisture retention and as a skin softener. Hexapeptide-11, an isolate of the yeast *Sacchamyces Cerevisae*, may be added to increase molecular integration within the dermal-epidermal junction, and thereby increase resistance within it to mechanical distortion.

As used herein an "expression line" is a wrinkle which is caused by repetitive flexion, distortion, and muscle fiber micro-contractions within the skin. Expression lines are either static or dynamic and they are associated with a damaged dermis layer.

As used herein, "preferred peptides" refers to the naturally occurring peptides, synthesized peptides, and commercially available compositions that contain peptides that have been known to affect the dermal rejuvenation required of this invention.

As used herein, the "preferred commercial composition" refers to a pre-formulated composition containing the preferred peptides and one or more additional skin care actives in an inert cosmetic base.

As used herein, "muscle relaxant" refers to the naturally occurring or, synthesized substances that have the ability to reduce the tonus or inhibit the reflex contraction of muscle fibers in human dermal and subdermal tissues.

As used herein, "preferred peptides" refers to the naturally occurring or, synthesized peptide molecules that have the ability to stimulate and rejuvenate and restore the formative layers of the upper dermis to replenish the collagen matrix, the formative cells and the intercellular ground substance of aged or environmentally damaged skin.

As used herein, the term "inert cosmetic base" refers to a medically suitable carrier that is safe for topical application to the cutaneous tissue of the face, has good cosmetic properties, is compatible and un-reactive with the actives of the present invention and any other components, and is non-toxic. It is necessary that the carrier be inert in the sense of not bringing about a deactivation of critical ingredients or the other active agents and in the sense of not bringing about any adverse effect on the skin to which it is applied. The inert cosmetic base percentage is from about 50% to about 99.99%, preferably about 70% to about 99.9%. The inert cosmetic base may be in the form of a gel, serum, paste, cream, ointment or lotion. In addition, the cosmetic base must be a suitable medium for inclusion of additional active or inert ingredients. Topical application is facilitated and, in some cases, additional therapeutic effects are provided as might be brought about, e.g., by moisturizing of the affected skin areas. Suitable carriers include water, alcohols, oils and the like, chosen for their ability to dissolve or disperse the active ingredients at concentrations of active ingredients most suitable for use in the therapeutic treatment. Generally, even low concentrations of active ingredients in an inert cosmetic base will be suitable, requiring only that more frequent topical application be resorted to.

As used herein, the "additional skin care actives" refers to a safe and effective amount of at least one additional active ingredient selected from the group consisting of anti-oxidants, anti-inflammatory, dermal matrix precursors, skin circulation promoters, vitamins, moisturizers, moisture retainers, skin softeners, anti-aging and anti-wrinkle preventives, cellular renewal agents, muscle relaxing peptides, moderate to slow acting muscle relaxants and healing agents. The additional skin care actives as described herein were selected according to the criteria that they be compatible with and enhance the efficacy of the final composition.

The additional skin care actives useful herein can be categorized by the benefit they contribute and/or by their mode of action. However, the actives can in some instances provide more than one benefit or operate via more than one mode of action. Thus, the classifications herein are made for the sake of convention and are not intended to solely limit the active agent to that particular application or applications listed. (Reference for herbal constituents from Duke, JA, CRC Handbook of Medicinal Herbs, CRC Press, Boca Raton, Fla., 1985, 110-1); also referenced (The 5th edition (1995) of the "International Cosmetic Ingredient Dictionary", edited by the American industrial association CTFA) lists about 300 plants which are added as active ingredients to cosmetic agents in various formulations.

The additional skin care actives preferably include, but are not limited to: marine collagen, allantoin, hydrolyzed wheat protein, green tea extract, *Centella asiatica*, dexapanthenol or pantothenic acid, dipeptide diaminobutyroyl benzalamide diacetate, lycopene, superoxide dismutase, and hyaluronic acid. Less preferable substitutions and/or additions may be made with the following additional skins care actives: pycnogenol, vitamin K, *Juglans regia* seed extract, *Fagus sylvatica* bud extract, hibiscus flower extract, water lily extract, extract isolates of yeast, i.e. *Sacchamyces cerevisae*, and lecithin.

As used herein the term "improves smoothness appearance" means that the visible appearance of the skin surface during both the contraction phase of facial expressive muscles and the relaxation phase is improved as determined by visual inspection with the naked eye.

Alternative physiologically acceptable mediums in which the compounds according to the invention can be used, as well as the components thereof, their amount, the galenic form of the composition and its preparation mode, can be selected by the person of the art on the basis of his/her general knowledge and depending on the type of the desired composition. For example, one or more of the additional skin care actives as described herein may be added to create expression line compositions that are more ideally suited for a specific skin type and skin condition that may co-exist with expression lines.

The sequence required for adding the *Acmella oleracea* extract during the manufacturing process varies according to the particular formulation being made and can be successfully carried out by those experienced in the art. In the preferred embodiment *Acmella oleracea* extract is added to the matrix repair serum containing Matrixyl™ 3000; said peptide formulation contains 5% by volume Matrixyl™ 3000. *Acmella oleracea* extract is added as a final component so that the final volume of the combined formulation contains 6% of the extract. To obtain a cosmetic composition exhibiting the above mentioned properties, the extract of the invention is used in the form of an ethanolic solution, said solution having a minimum concentration of 50 mg/l of the active molecule spilanthol. Spilanthol is the molecule that has been identified within the *Acmella oleracea* extract as having myo-suppressing activity. Detailed description of the additional skin care actives are as follows:

Adjunctive Anti-Cholinergic Peptides—

Two anti-cholinergic peptides that have muscle inhibitory properties are suitable for inclusion in this art. a) SYN®-AKE (Pentapharm, Ltd. Switzerland), is a synthetic copy of snake venom (of the Temple viper, *Tropidolaemus wagleri*), and it is a reversible antagonist of the neuromuscular post-synaptic nicotinic acetylcholine receptor. It is identified by the chemical name dipeptide diaminobutyroyl benzalamide diacetate. While its action is not nearly as rapid as the *Acmella oleracea* extract, SYN®-AKE is advantageous to this art because it has profound inhibitory effects on the expression lines and folds particularly of the forehead. b) Acetyl hexapeptide-3 has anti-cholinergic action, however the effects take up to 30 days on average before a visible reduction in wrinkles can occur. Accordingly, both SYN®-AKE and Acetyl hexapeptide-3 are the less preferred muscle relaxants to be used in the present art. A safe and effective amount of anti-cholinergic peptides may be added to the present composition, preferably, from about 0.1% to about 30%, more preferably from about 0.5% to about 20%, still more preferably from about 0.5% to about 10%, by weight of the composition formed.

Anti-oxidant Active a) Green tea extract is derived from the leaf of *Camellia sinensis*. It is a potent anti-oxidant that improves micro-circulation and it is a strong anti-inflammatory. Green tea also has good astringent properties due to a high content of tannic acid, and it is thus suitable to use in the treatment of under eye swelling such as eye creams. b) Pycnogenol extract (proanthocyanidine) is obtained from the bark of the French maritime pine tree. The extract is a potent anti-oxidant that also improves microcirculation, and thus increases blood flow in the lower dermis. By strengthening the arteries and veins against micro-leakage of blood constituents pycnogenol prevents discoloration of the skin. It is quickly absorbed in the skin and purportedly is retained for as long as 72 hours. Pycnogenol improves elasticity and smoothness of the skin by binding to collagen and elastin. The value of pycnogenol as a topical agent is described in the prior art in Lerner (U.S. Pat. No. 5,470,874). c) Lycopene, superoxide dismutase. A safe and effective amount of anti-oxidant active may be added to the present composition, preferably, from about 0.1% to about 30%, more preferably from about 0.5% to about 20%, still more preferably from about 0.5% to about 10%, by weight of the composition formed.

Circulation Promoter— a) Vitamin K (phytonadione) is an important factor in blood coagulation and promotes micro-circulation via its effect of healing broken and enlarged capillaries. It has been shown to reduce purpura (small bluish discolorations from bleeding vessels) in the skin following laser surgery. b) Hibiscus flower extract reduces dark circles and puffiness of the eyes by improving microcirculation in capillary vessels. It also inhibits the mechanical factors responsible for the appearance of expression lines on the face. A method for employing hibiscus extracts is described by Pauly et al., (U.S. Pat. No. 6,379,719). A safe and effective amount of a circulation promoting active may be added to the present composition, preferably, from about 0.1% to about 30%, more preferably from about 0.5% to about 20%, still more preferably from about 0.5% to about 10%, by weight of the composition formed.

Vitamins a) Dexapanthenol (vitamin B5, panothenic acid) facilitates penetration of large molecules. facilitates permeation of the epidermis; allows the skin's repair systems to function properly; B5 is known to help with tissue repair; commonly found in liver, eggs, dried brewers yeast. As known to those skilled in the art, (U.S. Pat. No. 5,554,647) topical administration of Vitamin B5 improves skin barrier function. b) Vitamin C has merit for its ability to promote collagen synthesis and it acts as a natural sunscreen. It is a free radical scavenger and has been shown to neutralize free oxygen radicals and other environmental toxins that damage the collagen matrix. Examples of Vitamin C derivatives are magnesium ascorbo-palmitate, L-ascorbic acid, tetrahexyldecyl ascorbate, sodium ascorbyl phosphate, ascorbyl phosphate. c) Vitamin E, in either a fat soluble or water soluble forms, is also a scavenger of free radical oxygen. It also potentiates the free radical scavenger effects of Vitamin C. d) Vitamin A (retinoids) and derivatives thereof, Idebenone, Ubiquinone may also be included. A safe and effective amount of a vitamin active may be added to the present composition, preferably, from about 0.1% to about 30%, more preferably from about 0.5% to about 20%, still more preferably from about 0.5% to about 10%, by weight of the composition formed.

MMP (Matrixmetalloproteinase) Inhibitors

Substances that prevent the degradation of collagen n aging skin are suitable additions tot his art. Examples include aspirin, glucocorticoids, Vitamin D3, hydoxamates, hydroxyurea derivatives, tetracyclines and derivatives thereof, and mixtures thereof. Skin Soothing and Skin Healing Actives Skin soothing or skin healing actives that are suitable for use herein include panthenoic acid derivatives (including panthenol, dexpanthenol, ethyl panthenol), allantoin, and comfrey. a) Allantoin softens smoothes and calms skin irritations, moistures and increases the healing of damaged epidermis. Allantoin is a commonly used healing agent by practitioners of the art. A suitable source of allantoin is Majestic Mountain Sage, USA. b) Comfrey extract is recognized for its skin soothing and healing properties in Duggan (U.S. Pat. No. 6,583,184). Derived from the root and leaves of *Symphytum officinale* the plant extract encourages cell growth and is easily absorbed through the skin. It has anti-inflammatory, astringent, and emollient properties. It is thought to stimulate the growth of healthy tissue due to its content of allantoin. Also, its high mucilage content acts as a skin soother and moisturizer. A suitable example of a comfrey extract is available from Cosmetochem under the trade name HERBASOL™. It is an extract obtained from comfrey herbs in approximately 60:40 v:v water in propylene glycol solution. It is about 3.5% to 5.5% active. c) Water Lily extract (*Lilium candidum*) has soothing properties, relieves irritations, and retards the substances responsible for premature skin aging, such as: free radicals, elastasis, cyclooxygenase and hyaluronidase. As shown in a teaching by Yamakai, et al. (U.S. Pat. No. 6,878,378), water lily extract accelerates ceramide production. This creates a more intact lipid barrier with human keratinocytes, and thus retains moisture within the epidermis. A safe and effective amount of a skin soothing or skin healing active may be added to the present composition, preferably, from about 0.1% to about 30%, more preferably from about 0.5% to about 20%, still more preferably from about 0.5% to about 10%, by weight of the composition formed.

Cell Renewal Agents

*Centella Asiatica* increases cell renewal and circulation. The active triterpenes within this herb have been shown to have a modulating effect on the development and metabolism of connective tissue. The activity is mediated by the effects on fibroblasts and of two amino acids relevant for collagen formation, alanine and proline. Methods describing the use of *Centella asiatica* in cosmetic preparations are described in Singh-Vema (U.S. Pat. No. 6,261,605). A safe and effective amount of a cell renewal active agent may be added to the present composition, preferably, from about 0.1% to about 30%, more preferably from about 0.5% to about 20%, still more preferably from about 0.5% to about 10%, by weight of the composition formed.

Skin Softener a) Hydrolyzed wheat protein is a skin softener of the preferred embodiment. This biopolymer obtained from the endosperm of wheat germs has properties similar to collagen. It forms an adhesive network on the skin surface into which water and lipids are incorporated and slowly released.

b) Lecithin (phospholipid) is a component of lipids and plant oils, strengthens the skin barrier against loss of moisture, facilitates penetration of many ingredients into the skin, and it is a natural emollient. A safe and effective amount of a skin softener active agent may be added to the present composition, preferably, from about 0.1% to about 30%, more preferably from about 0.5% to about 20%, still more preferably from about 0.5% to about 10%, by weight of the composition formed.

Dermal Matrix Precursors

Marine collage (manufactured by CTPP, France) has a molecular weight under 700; efficient adsorption through the skin and an important source of hydroxyproline amino acid. As described in Wolfinbarger (U.S. Pat. No. 6,916,910), marine collagen can be processed into an exceptionally versatile ingredient for cosmetic use; said preparation includes telopeptides that contain type V fibrillar collagen. A safe and effective amount of a dermal matrix precursor may be added to the present composition, preferably, from about 0.1% to about 30%, more preferably from about 0.5% to about 20%, still more preferably from about 0.5% to about 10%, by weight of the composition formed.

Anti-aging/Anti-wrinkle a) *Fagus sylvatica* extract, known as Gatuline® RC (manufactured by Gattefosse, France) is a moisturizer and increases protein synthesis in the keratinocytes of nutrients and regulating peptides (keratin and filaggrin). Gatuline® RC is an extract of the bud or young shoot of the beech tree, *Fagus sylvatica*. As shown by Nakayama et al. (U.S. Pat. No. 6,531,165), the extract exhibits superior collagen producing effects via activation of the extracellular matrix.

b) *Juglans regia* seed extract known as Gatuline® Age Defense (manufactured by Gattefosse, France) is an anti-wrinkle and environmental stress protective specifically indicated for the eyes and lips. The prior art of Laforet (U.S. Pat. No. 6,395,261) discloses that this is an extract produced in aqueous solvent. This extract has ability to protect skin cells against oxidative stress induced by UVB radiation, stimulate the synthesis of proteins by cells of the dermis and epidermis, inhibit inflammation in skin cells, stimulate the synthesis of glycosaminoglycans by dermal fibroblasts, inhibit collagenase in skin cells, inhibit elastase in skin cells, and inhibit apoptosis in skin cells. c) Hexapeptide-11 is a low molecular weight fragment isolated from a yeast, *Sacchamyces Cerevisae* (U.S. Pat. No. 6,531,132) (marketed as Peptamide-6™ by Arch Personal Care Products, USA). This peptide protects the dermo-epidermal junction against the effects of cutaneous aging by stimulating the synthesis of the anchoring molecules such as the integrines, the fibronectine and the collagens IV and VII. The extract promotes cohesion between the deep formative elements of the skin, maintains tissue repair via increasing the resistance of the dermo-epidermal junction to mechanical deformation. A safe and effective amount of a anti-aging/anti-wrinkling agent may be added to the present composition, preferably, from about 0.1% to about 30%, more preferably from about 0.5% to about 20%, still more preferably from about 0.5% to about 10%, by weight of the composition formed.

Botanical Dermal Matrix Stimulator

*Siegesbeckia Orientalis* Extract is obtained from the herb of the same name. The herb has been used for centuries externally to soothe inflammation and stimulate wound healing, which it does by tissue regeneration from collagen matrix build-up. *S. Orientalis* increases the normal appearance of damaged skin, i.e. scars, and restores elasticity to the skin by reorganizing the damaged and disorganized collagen fibers. The extract has been shown to inhibit collagenase, and protect the skin from UV induced erythema. A safe and effective amount of a anti-aging/anti-wrinkling agent may be added to the present composition, preferably, from about 0.1% to about 30%, more preferably from about 0.5% to about 20%, still more preferably from about 0.5% to about 10%, by weight of the composition formed.

Whitening Agents

Embelica, Hydroquinone, Arbutin, Kojic acid A safe and effective amount of a anti-aging/anti-wrinkling agent may be added to the present composition, preferably, from about 0.1% to about 30%, more preferably from about 0.5% to about 20%, still more preferably from about 0.5% to about 10%, by weight of the composition formed.

Anti-inflammatory

Boswella is an Ayurvedic herb that is the source of boswellic acid which has been found to have inhibitory action on the inflammatory process. A phyto-complex combining boswellic acid and manganese (developed by L'Oreal Corporation, France) is said to reduce the appearance of expression lines and wrinkles within three weeks of use by reducing micro-contractions of muscle fibers in skin. A safe and effective amount of a anti-aging/anti-wrinkling agent may be added to the present composition, preferably, from about 0.1% to about 30%, more preferably from about 0.5% to about 20%, still more preferably from about 0.5% to about 10%, by weight of the composition formed.

Moisture Retainer/Binder

Chitosan is a complex polysaccharide derived from shellfish exoskeletons. Chitosan forms a protective, moisturizing, elastic film on the surface of the skin that has the ability to bind together other ingredients; thus enhancing bioactivity and effectiveness of cosmetic compositions. Aloe vera extract is a polysaccharide derived from the leaf of the aloe plant. The extract is soluble in water and is a suitable base carrier.

It is preferable that the cosmetic administration of the invention be comprised of a twice daily application for a period of one week of daily administration of the compound, more preferably two weeks, and most preferably at least a month of daily topical application with twice daily of administration of the invention over the month being even more preferable. Thereafter, daily applications should continue once daily for at least three months.

Data published by Sederma, S.A. states that after two months of application of a peptide formulation, i.e. Matryxil™ 3000 the surface area of the skin occupied by deep wrinkles was reduced by 45%. Their data does not differentiate between static wrinkles and expression line type wrinkles. The following experiment by the inventor indicates an accelerated reduction in the appearance of expression line wrinkles.

EXAMPLE 1

Trial

The A/B trial: 16 female subjects who are clinic patients of the applicant participated in a study comparing the invention of this application, the formula for the invention devoid of a muscle inhibitor, and a control. Each subject was selected upon the condition of having pronounced expression lines of their eyes, bilaterally and latero-inferiorly i.e. "crow's feet". The subjects were divided into 2 groups. Group A had 8 participants and group B had 8 participants. The subjects in each group were each given two vials of serum. Group A: One vial was the formula as in example no. 2 minus *Acmella oleracea* extract while the other vial was the control, i.e. the formula as in example no. 2 minus the *Acmella oleracea* and the peptide constituents. Group number B: One vial was the invention formula as in example no. 2., and one was the control. The control served as a reference for comparison to the test side where the active formulas were applied.

The vials are labeled #1 and #2, and the contents of each vial were known to the applicant and to the subjects. The subjects from each group were instructed to select one vial for daily application to one side of the face and to apply the control vial only to the opposite side. The control side served as a constant reference for visually judging the degree of improvement from the active formulations. The subjects were instructed to apply the serums twice daily for the duration of the 60-day trial. They were instructed to observe the appearance of the expression lines bilaterally after the first 10 minutes following the initial application. Thereafter, they were instructed to observe the appearance of the expression lines bilaterally at 7-day intervals and to record differences in the appearance of skin smoothness while the facial skin was expressionless, and then a second time while making a mild smile expression. The same doses were applied between each test area, but here was no assurance that the same dose did not vary from one subject to the next.

The C/D trial: A second was done using 13 females and one male subject. Once again each subject was selected upon the condition of having pronounced expression lines bilaterally and lateral or latero-inferiorly to their eyes. The subjects were divided into 2 groups. Group C had 6 subjects and group D had 7 subjects. Each subject in group C was given two vials. One vial contained the formula as in example no. 2, but it was devoid of the peptides. The other vial was a control, i.e. the formula as in example no. 2 minus the *Acmella oleracea* and the peptide constituents. Each subject in group D was given two vials. One vial contained the invention formula as in example no. 2. The other vial was a control, i.e. the formula as in example no. 2 minus the *Acmella oleracea* and the peptide constituents. The vials were labeled #1 and #2, and the contents of each vial were known to the applicant and to the subjects. The same doses were applied between each test area, but there was no assurance that the same dose did not vary from one subject to the next.

The instructions for group C and D had an added step in that each 7-day interval was to be followed by a 48 hour "wash" period, wherein no composition was applied to the area after the skin was washed thoroughly. Immediately following this period a second observation was recorded.

Mention should be made of the method of measuring expression lines. Mindful of the fact that expression lines are dynamic wrinkles, and thus are subject to a fluctuation in their dimensions during the contraction-relaxation phase of muscle activity, standard technologies of measurement are not applicable in the trials as described herein (Simulation of Skin Aging and Wrinkles with Cosmetics Insight, Laurence Boissieaux, et al., University of Geneva, 2000). For example, a very shallow wrinkle may become a very pronounced one during expression muscle, activity and thus measuring it during a resting state is misleading. Therefore, the most practical method of determining whether expression lines are improved by the composition herein is by having the subjects make visual comparisons of skin smoothness appearance, and by using the lines on the opposite side of the face as a point of reference. The instructions given to the subjects were to apply one drop of serum from #1 vial to the crow's feet on the right side of the face and one drop of serum from the #2 vial to the same area on the left. Clinic patients served as their own evaluators. Both test subjects and evaluators were instructed to grade the expression lines according to a scale from 0 through 5. Each increase in the numerical grade represented a change in visual smoothness and each unit number corresponded to a percentage increase of twenty percent in visual improvement of appearance.

The state of the skin was observed visually and evaluated based on the following evaluation criteria.
(Evaluation Criteria)
0=no change
1=Slightly improved
2=Improved
3=Greatly improved still noticeable
4=Extremely improved, barely noticeable
5=Not noticeable
The Data of A/B Trial:

The results of the A/B trial were as follows: Seven of eight participants in the B group observed a significant improvement in the appearance of their expression lines within the first 10 minutes following application, whereas the A group none of the participants reported a change until 21 days. Group number A and B both had a steady improvement in the smoothness appearance of crow's feet expression lines during static and mild expression on side that the invention composition was used. On the side where the formula was minus the *Acmella oleracea* extract there was a significant improvement observed at the $35^{th}$ day and this continued until the end of the 60-day trial. However, on the side where the vial contained the invention formula the smoothness appearance (of both the static and dynamic expression lines) improved more rapidly; a 25% improvement was observed immediately and about 50% improvement occurred at the $23^{rd}$ day. It took nearly 32 days for the formula devoid of *Acmella* to match the invention in smoothness appearance. At 52 days the formula without *Acmella* was equal to the invention formula in improving smoothness appearance.

The conclusion is that the muscle relaxant in the invention formula increased smoothness appearance of the expression lines at a faster rate then the formula devoid of the muscle relaxant. The initial rapid onset of expression line reduction was due to the *Acmella oleracea* extract.

Sederma (US Pub no. 20040132667) indicates that after applying Matrixyl™ 3000 product for 60 days there is a measurable reduction up to a 60% (and a visual improvement of 45% surface area smoothness on average) in the surface area occupied by deep wrinkles. In contrast the A/B trial shows that with the invention formula this magnitude of improvement is achieved between 35 and 42 days.

The Data of C/D Trial:

Data from trial C and D showed that there was a steady increase in static and dynamic expression line smoothness appearance over a 37 day period, but that immediately following the 48-hour wash period the formula devoid of peptide had a sharp reversal in smoothness appearance. Conversely, the invention composition had smoothness appearance-following the wash—that was nearly the same as the peptide free side until the 28th day; after 37 days the invention caused smoothness appearance to be maintained following the wash period. Smoothness appearance by the invention formula was then maintained for the remainder of the trial. In addition, the smoothness appearance improved nearly 50% by the 37$^{th}$ day, which is significantly faster than reported for Matrixyl™ and Matrixyl™ 3000 when they were tested by the manufacturer as a single actives in inert carriers (see website www.crodausa.com).

The conclusion from this A/B trial was that *Acmella oleracea* may increase smoothness appearance at a faster rate, but as shown by the C/D trial the inclusion of the Matrixyl™ 3000 was essential for the level of improvement to be stabilized.

Also, the magnitude of increased smoothness appearance was greater in this trial then has been reported in the published literature.

Figure 2:
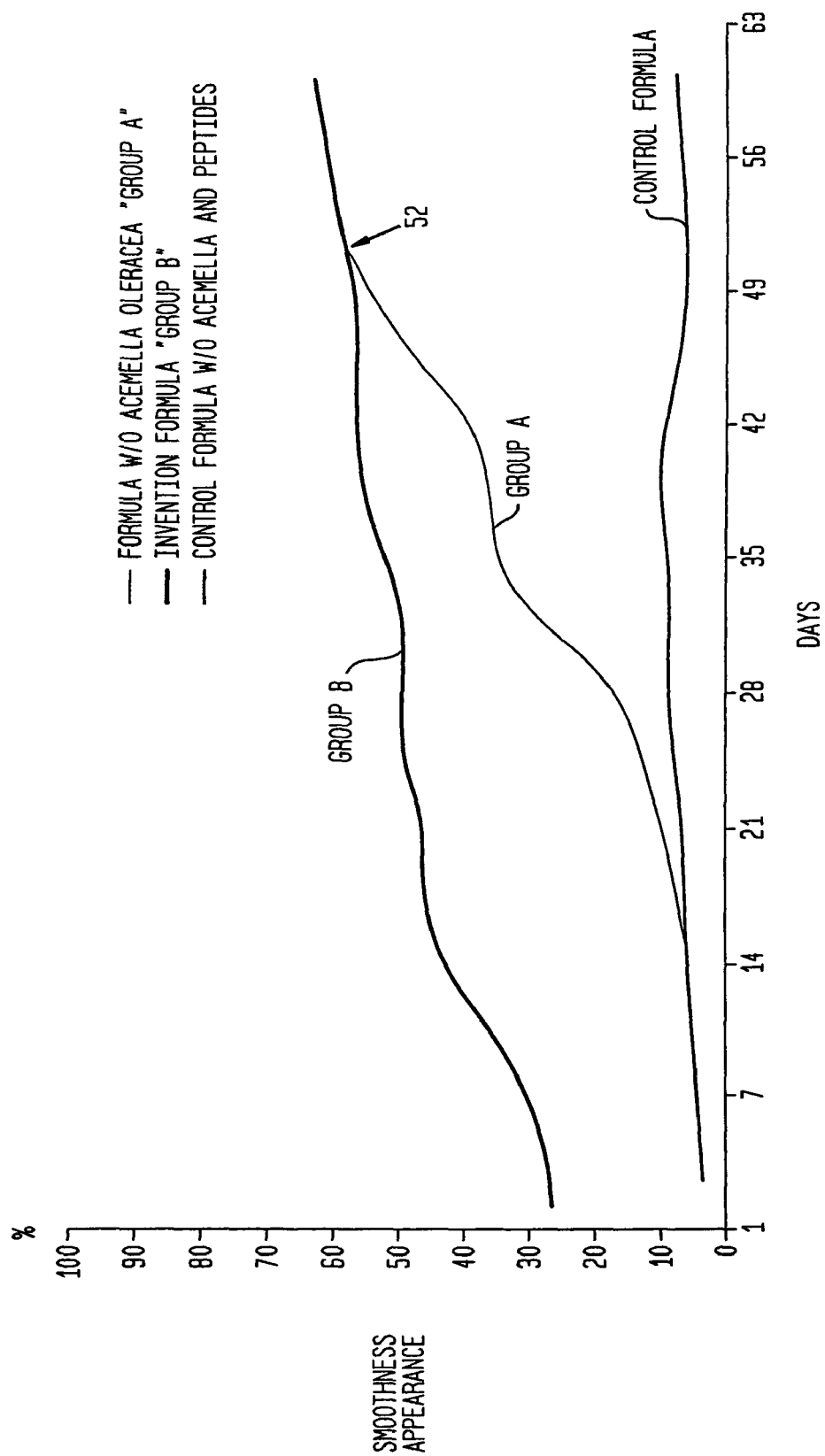

The results of the test trials are shown in FIGS. 1-2. In FIG. 1, the Group C and D trials are shown. FIG. 2 shows the Group A and B trials.

EXAMPLE 2

Expression Line Gel

In the following example, and throughout this example all percentages are by weight and based on the weight of the final composition. All mixing is carried out at ambient temperature.

Preparation of a Topical Gel.

| INCI Name | % weight |
|---|---|
| Phase I | |
| *Aloe Vera* dry extract | 1.0 |
| Germaben ® II | 1.0 |
| Demineralized water | 74.0 |
| Phase 2 | |
| Beheneth-25 Methacrylate Copolymer* | 7.0 |
| Triethanolamine | 1.5 |
| Phase 3 | |
| Matrixyl ™ 3000 | 8.0 |
| *Centella Asiatica* | 1.5 |
| Phase 4 | |
| *Acmella Oleracea* extract (and) water (and) alcohol | 6.0 |
| | 100.00% |

*sold by Rohm & Haas under the name Aculyn 28.

Phase 1

Blend Aloe powder with distilled water. Stir moderately until fully blended and no Aloe powder is visible. Add Germaben II preservative. Stir 2-3 minutes.

Phase 2

Add Beheneth-25 Methacrylate Copolymer to Phase 1. Stir thoroughly for 10 minutes at ambient temperature. Add triethanolamine. Stir vigorously until a clear and consistent gel results.

Phase 3

At ambient temperature add the components of Phase 3 one by one into Phase 1, 2 and stir slowly for 15 minutes.

Phase 4

Measure volume of composition from phase 1, 2, 3 and replace 6% by volume with *Acmella oleracea* extract (Gatuline® expression extract in water). Stir slowly for 10 minutes at ambient temperature.

The trials herein were carried out using the basic composition of Example 2 that contained preferred elements of this invention and only one active ingredient. The intent was to observe in a simple form the influence that the invention had upon the skin without the additive effects of multiple active ingredients.

The inclusion of multiple additional active ingredients are not to be regarded as a departure from the spirit and scope of the invention. All such modifications would be obvious to one skilled in the art are thus intended to be included within the scope of the following claims.

What is claimed is:

1. A skin care composition that improves the appearance of expression lines of the human face comprising:
   a. a muscle relaxant obtained from *Acmella oleracea* flower extract;
   b. a safe and effective amount of dermal stimulating peptides selected from the group consisting of palmitoyl tetrapeptide, palmitoyl tripeptide, palmitoyl oligopeptide, palmitoyl pentapeptide, and mixtures thereof;
   c. a safe and effective amount of at least one additional skin care active selected from the group consisting of antioxidants, anti-inflammatories, dermal matrix precursors, skin circulation promoters, vitamins, moisturizers, and skin softeners, wrinkle preventives, botanical dermal matrix builders, anti-cholinergic peptides, metalloproteinase inhibitors, and healing agents; and
   d. a dermatologically acceptable inert cosmetic base.

2. A skin care composition that improves the appearance of expression lines of the human face comprising:
   a. spilanthol as an active isolate of *Acmella oleracea* extract;
   b. a safe and effective amount of dermal stimulating peptides selected from the group consisting of palmitoyl tetrapeptide, palmitoyl tripeptide, palmitoyl oligopeptide, palmitoyl pentapeptide, and mixtures thereof;
   c. a safe and effective amount of at least one additional skin care active selected from the group consisting of *Centella asiatica*, green tea, hydrolyzed wheat protein, marine collagen, allantoin, dexapanthenol, acetyl hexapeptide-3, dipeptide diaminobutyroyl benzylamide diacetate, lycopene, palmitoyl pentapeptide, pycnogenol and hyularonic acid ; and
   d. a dermatologically acceptable inert cosmetic base.

3. A skin care composition that improves the appearance of expression lines of the human face comprising:
   a. spilanthol as an active isolate of *Acmella oleracea* extract;
   b. a safe and effective amount of dermal stimulating peptides selected from the group consisting of palmitoyl tetrapeptide, palmitoyl tripeptide, palmitoyl oligopeptide, palmitoyl pentapeptide, and mixtures thereof; and
   c. a dermatologically acceptable inert cosmetic base.

4. A skin care composition that improves the appearance of expression lines of the human face comprising:
  a. a botanical extract containing the myo-inhibitory molecule known as spilanthol ;
  b. a safe and effective amount of a dermal stimulating peptide that can effect an increase in collagen matrix synthesis;
  c. a safe and effective amount of at least one additional skin care active selected from the group consisting of anti-oxidants, anti-inflammatories, dermal matrix precursors, skin circulation promoters, vitamins, moisturizers, and skin softeners, wrinkle preventives, skin botanical dermal matrix builders, anti-cholinergic peptides, metalloproteinase inhibitors, and healing agents; and d. a dermatologically acceptable inert cosmetic base.

5. A skin care composition that improves the appearance of expression lines of the human face comprising an extract of *Acmella oleracea*;
  a. a safe and effective amount of a dermal stimulating peptide that can effect an increase in collagen matrix synthesis;
  b. a safe and effective amount of at least one additional skin care active selected from the group consisting of anti-oxidant, anti-inflammatory, dermal matrix precursor, skin circulation promoter, vitamin, moisturizer, and skin softener, wrinkle preventive, botanical dermal matrix builder, anti-cholinergic peptide, metalloproteinase inhibitor, and healing agent; and
  c. a dermatologically acceptable inert cosmetic base.

6. A skin care composition that improves the appearance of facial expression lines by altering the cellular dermal matrix of skin comprising an extract of Acmella oleracea flower and;
  a. a safe and effective amount of a dermal stimulating peptide that can effect an increase in collagen matrix synthesis;
  b. a safe and effective amount of at least one additional skin care active selected from the group consisting of anti-oxidant, anti-inflammatory, dermal matrix precursor, skin circulation promoter, vitamin, moisturizer, and skin softener, wrinkle preventive, botanical dermal matrix builder, anti-cholinergic peptide, metalloproteinase inhibitor, and healing agent; and
  c. a dermatologically acceptable inert cosmetic base.

* * * * *